United States Patent
Ameri et al.

(10) Patent No.: US 9,173,924 B2
(45) Date of Patent: Nov. 3, 2015

(54) STABLE GLUCAGON PEPTIDE FORMULATIONS

(71) Applicant: ZP OpCo, Inc., Fremont, CA (US)

(72) Inventors: Mahmoud Ameri, Fremont, CA (US); Peter E. Daddona, Menlo Park, CA (US); Yi Ao, Palo Alto, CA (US)

(73) Assignee: ZP OPCO, INC., Fremont, CA (US)

( * ) Notice: Subject to any disclaimer, the term of this patent is extended or adjusted under 35 U.S.C. 154(b) by 0 days.

(21) Appl. No.: 14/466,461

(22) Filed: Aug. 22, 2014

(65) Prior Publication Data

US 2015/0057605 A1    Feb. 26, 2015

Related U.S. Application Data

(60) Provisional application No. 61/868,969, filed on Aug. 22, 2013.

(51) Int. Cl.

| | |
|---|---|
| *A61K 38/26* | (2006.01) |
| *A61M 37/00* | (2006.01) |
| *A61K 9/00* | (2006.01) |
| *A61K 47/24* | (2006.01) |
| *A61K 47/26* | (2006.01) |
| *A61K 47/18* | (2006.01) |
| *A61K 47/12* | (2006.01) |
| *A61K 9/70* | (2006.01) |

(52) U.S. Cl.
CPC ............... *A61K 38/26* (2013.01); *A61K 9/0021* (2013.01); *A61M 37/0015* (2013.01); *A61K 9/7023* (2013.01); *A61K 47/12* (2013.01); *A61K 47/183* (2013.01); *A61K 47/24* (2013.01); *A61K 47/26* (2013.01); *A61M 2037/0023* (2013.01); *A61M 2037/0046* (2013.01); *A61M 2037/0053* (2013.01); *A61M 2037/0061* (2013.01)

(58) Field of Classification Search
None
See application file for complete search history.

(56) References Cited

U.S. PATENT DOCUMENTS

| | | | | |
|---|---|---|---|---|
| 5,652,216 | A  * | 7/1997 | Kornfelt et al. | 514/11.7 |
| 2008/0234200 | A1 | 9/2008 | Quay et al. | 514/12 |
| 2010/0221305 | A1 * | 9/2010 | Ameri et al. | 424/443 |
| 2011/0097386 | A1 * | 4/2011 | Steiner et al. | 424/450 |
| 2012/0046225 | A1 * | 2/2012 | Prestrelski et al. | 514/6.8 |
| 2012/0071817 | A1 | 3/2012 | Ward et al. | 604/65 |
| 2012/0302502 | A1 * | 11/2012 | Botti et al. | 514/11.7 |
| 2014/0378381 | A1 * | 12/2014 | Chen et al. | 514/11.7 |

FOREIGN PATENT DOCUMENTS

| | | | |
|---|---|---|---|
| WO | 2007/121411 | 10/2007 | |
| WO | 2013/101749 | 7/2013 | A61K 9/113 |

OTHER PUBLICATIONS

International Searching Authority, International Search Report for International Application No. PCT/US2014/052326 mailed Dec. 22, 2014 along with the Written Opinion, 24 pages.

* cited by examiner

*Primary Examiner* — Jeffrey E Russel

(74) *Attorney, Agent, or Firm* — Sunstein Kann Murphy & Timbers LLP

(57) ABSTRACT

There is provided glucagon formulations suitable for preparing coatings on microneedle patches for the transdermal delivery of glucagon. The coated patches may be used for the treatment of low blood sugar in diabetic patients. Also provided are glucagon loaded patches, methods for their preparation, and methods of their use.

45 Claims, 16 Drawing Sheets

STABLE GLUCAGON PEPTIDE FORMULATIONS

CROSS-REFERENCE TO RELATED APPLICATIONS

This application claims priority to U.S. provisional application No. 61/868,969 filed Aug. 22, 2013, the contents of which are incorporated by reference herein in their entirety.

TECHNICAL FIELD

The present invention relates to drug delivery, and more particularly to formulations of glucagon for delivery through the skin.

BACKGROUND ART

Glucagon is produced in humans by the pancreas. Glucagon binds to specific receptors on liver cells and increases the release of glucose in the blood stream. Thus, it is used in the treatment of diabetes as a rescue medication when the blood sugar level drops too low.

Glucagon is a short peptide having 29 amino acids and a molecular weight of 3,483 kilodaltons (kDa). The sequence of amino acid in glucagon is:

```
His Ser Gln Gly Thr Phe Thr Ser Asp Tyr
1               5                   10

Ser Lys Tyr Leu Asp Ser Arg Arg Ala Gln
                15                  20

(SEQ ID NO: 1)
Asp Phe Val Gln Trp Leu Met Asn Thr
21              25              29
```

Glucagon has a highly helical conformation in the crystalline state, but forms a random coil in dilute solution with about 15% alpha helix at the C-terminus. At higher concentrations it generally precipitates and forms fibrils. Glucagon readily dissolved in aqueous solution at pH below 3 or above 9, but precipitates readily at pH between 4 and 8. Liquid formulations of glucagon are highly unstable, and undergo hydrolysis and deamidation at several positions (amino acid at position 3, 9, 15, 20, 21, and 24) and thus pharmaceutical preparations are generally provided in dual containers: powders of glucagon in one side and a liquid diluent in another. A solution of glucagon is then prepared just prior to use. Procedures generally undertaken to mitigate the instability of glucagon in liquid formulations include the use of solid dispersions, aprotic solvents, surfactants, processes conducted at low temperature, and packaging in dried form.

Dilute formulations have been prepared that are stable for up to 6 days and are useful for delivery with a pump (US2011/0097386). The concentration of glucagon in these formulations is between 0.8 mg/mL to 5 mg/mL and the pH is between 4 and 7. Stabilizing agents are a combination of both low concentrations of a surfactant such as 1 mg/ml LMPC and high concentrations of saccharide such as 45 mg/mL of glucose.

SUMMARY OF THE EMBODIMENTS

The invention comprises new formulations of glucagon suitable for transdermal delivery. Stable liquid formulations are described at high concentration of glucagon. These formulations do not form gels or fibrils and can be readily deposited onto substrates to form a uniform coating. Once deposited onto a substrate and dried, the glucagon in the coatings has improved stability over time. The glucagon can be readily reconstituted (such as with bodily fluids) without forming a gel. These formulations are thus suited for use as coatings on substrates such as microneedle patches for the transdermal delivery of glucagon for the treatment of low blood sugar.

In a first aspect of the invention, there is provided a liquid pharmaceutical formulation comprising 15-20% (w/w) of glucagon, 7.5-10% (w/w) of a stabilizing agent selected from either a cationic or neutral surfactant, 3.75-5% (w/w) of an amino acid, 3.75-5% (w/w) of an organic acid, and a pharmaceutically acceptable diluent; the formulation having a pH between 2 and 3. In some embodiments, the surfactant is a phospholipid. In some embodiments, the phospholipid is lyso-myristoyl phosphatidylcholine. In other embodiments, the surfactant is decanoyl sucrose. In yet other embodiments, the amino acid is selected from the group consisting of glutamine and glycine. In some embodiments, the organic acid is selected from the group consisting of methanoic acid, ethanoic acid, tartaric acid, malonic acid, glycolic acid, malic acid, gluconic acid, citric acid, caproic acid, benzoic acid, lactic acid, propionic acid, and sorbic acid. In certain embodiments, the pharmaceutical formulation has a viscosity in the range of 20-200 centipoise (cP).

In certain embodiments, the pharmaceutical formulation, the surfactant is decanoyl sucrose, the amino acid is glutamine and the organic acid is tartaric acid. In other embodiments, the surfactant is decanoyl sucrose, the amino acid is glycine and the organic acid is tartaric acid. In yet other embodiments, the surfactant is lyso-myristoyl phosphatidylcholine, the amino acid is glutamine and the organic acid is tartaric acid. Still in other embodiments, the surfactant is lyso-myristoyl phosphatidylcholine, the amino acid is glycine and the organic acid is tartaric acid.

In a second aspect of the invention, there is provided a solid pharmaceutical formulation comprising 40-50% (w/w) of glucagon or a glucagon-like peptide, 20-25% (w/w) of a stabilizing agent selected from either a cationic or neutral surfactant, 10-12.5% (w/w) of an amino acid, 10-12.5% (w/w) of an organic acid; the formulation having a pH between 2 and 3. In some embodiments, the surfactant is a phospholipid. In some embodiments, the phospholipid is lyso-myristoyl phosphatidylcholine. In other embodiments, the surfactant is selected from the group consisting of glucose, sucrose, trehalose, and dextrose substituted with a C8-C12 alkyl chain. In other embodiments, the surfactant is decanoyl sucrose. In some other embodiments, the amino acid is selected from the group consisting of glutamine and glycine. In some other embodiments, the organic acid is selected from the group consisting of methanoic acid, ethanoic acid, tartaric acid, malonic acid, glycolic acid, malic acid, gluconic acid, and citric acid.

In yet other embodiments, the surfactant is decanoyl sucrose, the amino acid is glutamine and the organic acid is tartaric acid. In other embodiments, the surfactant is decanoyl sucrose, the amino acid is glycine and the organic acid is tartaric acid. In other embodiments, the surfactant is lyso-myristoyl phosphatidylcholine, the amino acid is glutamine and the organic acid is tartaric acid. In other embodiments, the surfactant is lyso-myristoyl phosphatidylcholine, the amino acid is glycine and the organic acid is tartaric acid.

In a third aspect of the invention, there is provided a medical device for the delivery of a pharmaceutical agent through the skin, the device comprising an array of microneedles having coated thereon a liquid composition comprising 15-20% (w/w) of glucagon, 7.5-10% (w/w) of a stabilizing agent selected from either a cationic or neutral surfactant, 3.75-5% (w/w) of an amino acid, 3.75-5% (w/w) of an organic acid, and a pharmaceutically acceptable diluent; the formulation having a pH between 2 and 3. In some embodiments, the medical device carries a therapeutic dose of glucagon of either 1 mg for an adult dose, or 0.5 mg for a pediatric dose. In some embodiments, the surfactant is a phospholipid. In some embodiments, the phospholipid is lyso-myristoyl phosphatidylcholine. In other embodiments, the surfactant is selected from the group consisting of glucose, sucrose, trehalose, dextrose substituted with a C8-C12 alkyl chain. In other embodiments, the surfactant is decanoyl sucrose. In some other embodiments, the amino acid is selected from the group consisting of glutamine and glycine. In some other embodiments, the organic acid is selected from the group consisting of methanoic acid, ethanoic acid, tartaric acid, malonic acid, glycolic acid, malic acid, gluconic acid, and citric acid.

In a fourth aspect of the invention, there is provided a medical device for the delivery of a pharmaceutical agent through the skin, the device comprising an array of microneedles having coated thereon a solid composition comprising 40-50% (w/w) of glucagon or a glucagon-like peptide, 20-25% (w/w) of a stabilizing agent selected from either a cationic or neutral surfactant, 10-12.5% (w/w) of an amino acid, 10-12.5% (w/w) of an organic acid; the formulation having a pH between 2 and 3. In some embodiments, the medical device carries a therapeutic dose of glucagon of either 1 mg for an adult dose, or 0.5 mg for a pediatric dose. In some embodiments, the surfactant is a phospholipid. In some embodiments, the phospholipid is lyso-myristoyl phosphatidylcholine. In other embodiments, the surfactant is selected from the group consisting of glucose, sucrose, trehalose, dextrose substituted with a C8-C12 alkyl chain. In other embodiments, the surfactant is decanoyl sucrose. In some other embodiments, the amino acid is selected from the group consisting of glutamine and glycine. In some other embodiments, the organic acid is selected from the group consisting of methanoic acid, ethanoic acid, tartaric acid, malonic acid, glycolic acid, malic acid, gluconic acid, and citric acid.

In some embodiment, the solid formulation is such that once applied to the skin of a patient the coating is dissolved by the body fluids of the patient in less than 30 minutes. In other embodiments, the coating is dissolved by the body fluids of the patient in less than 20 minutes. In other embodiments, the coating is dissolved by the body fluids of the patient in less than 10 minutes.

In a fifth aspect of the invention, there is provided a process for coating a medical device comprising coating a liquid pharmaceutical composition according to the invention described herein onto a medical device and drying the pharmaceutical composition.

In a sixth aspect of the invention, there is provided methods of treating a patient having low blood sugar comprising applying the medical device having a solid formulation applied thereon according to the invention described herein to the skin of the patient. In some embodiments, a blood serum $C_{max}$ of glucagon is reached in less than 30 minutes. In other embodiments, a blood serum $C_{max}$ of glucagon is reached in about 10 min. In yet other embodiments, a blood serum $C_{max}$ of glucagon reaches at least 5 ng/mL. In other embodiments, a blood serum $C_{max}$ of glucagon reaches at least 10 ng/mL. In still other embodiments, a blood serum $C_{max}$ of glucagon reaches about 20 ng/mL.

In other embodiments, a blood serum $C_{max}$ of glucagon of at least 5 ng/mL is reached in less than 20 minutes following application of the device to the skin of the patient. In yet other embodiments, a blood serum $C_{max}$ of glucagon of at least 5 ng/mL is reached in about 10 minutes following application of the device to the skin of the patient. In yet other embodiments, a blood serum $C_{max}$ of glucagon of about 10 ng/mL is reached in about 10 minutes following application of the device to the skin of the patient. In still other embodiments, a blood serum concentration of glucagon is less than 10 ng/mL at about 60 minutes following application of the device to the skin of the patient.

In yet other embodiments, a blood serum $C_{max}$ of glucagon of at least 5 ng/mL is reached in less than 20 minutes and blood serum concentration of glucagon less than 10 ng/mL at about 40 minutes following application of the device to the skin of the patient. In still other embodiments, a blood serum $C_{max}$ of glucagon of at least 10 ng/mL is reached in less than 20 minutes and blood serum concentration of glucagon less than 10 ng/mL at about 30 minutes following application of the device to the skin of the patient.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
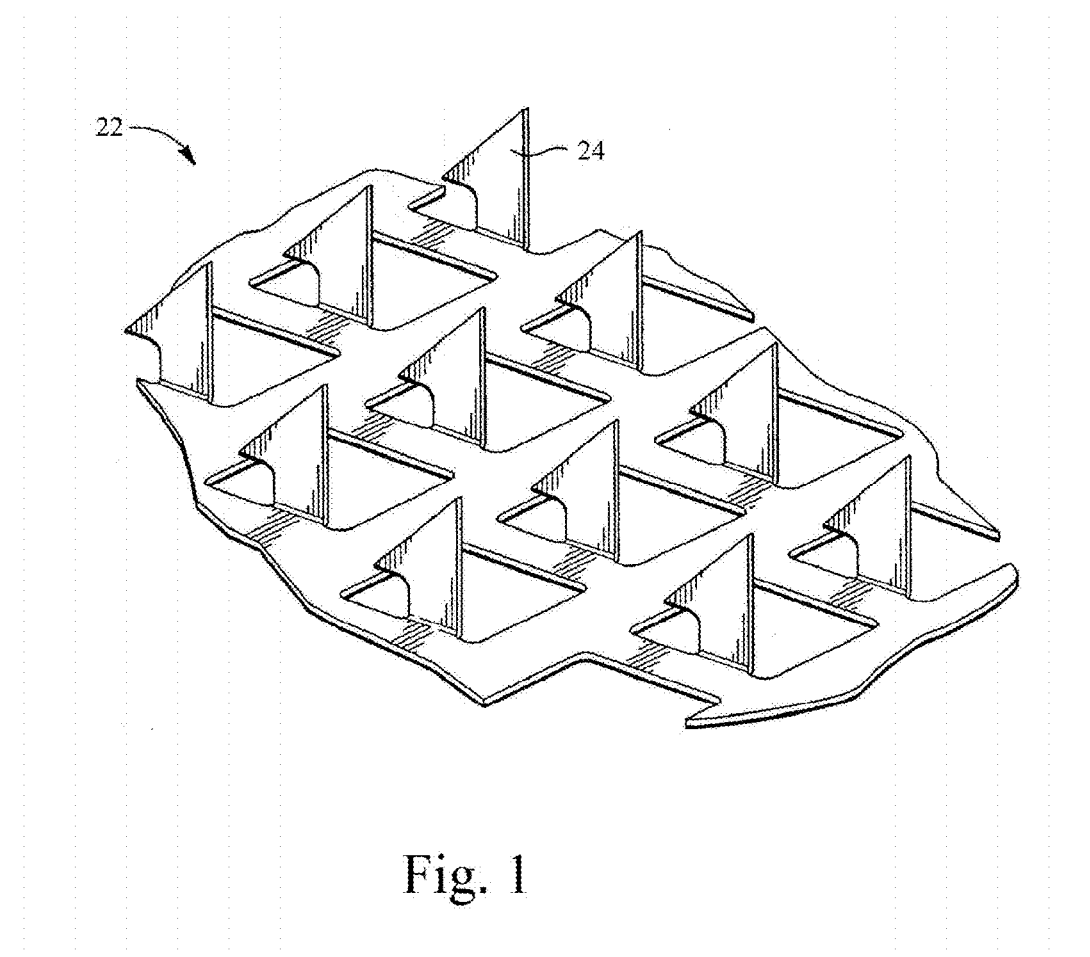
FIG. 1 is a perspective view of a portion of one example of a microneedle patch, according to the invention.

Definitions. Unless defined otherwise, all technical and scientific terms used in this description and the accompanying claims have the same meaning as commonly understood by one of ordinary skill in the art to which this invention belongs.

An alkyl saccharide according to the invention means a compound comprising a carbohydrate moiety of the type $R-C_xH_{2y+z}O_y$, wherein x and y are integers ranging from 3-12, z is a numeral ranging from -1 to 1, R may be an hydrogen or a linear or branched C1-C22 alkyl or alkyl groups saturated or partially unsaturated, including methyl, ethyl, propyl, butyl, pentyl, hexyl, heptyl, octyl-, nonyl-, decyl-, undecyl, dodecyl-, tridecyl-, tetradecyl-, pentadecyl-, hexadecyl-, heptadecyl-, octadecyl-, nondecyl-, eicosanyl-, heneicosanyl-, docosanyl-, ethoyl-, propoyl-, butoyl-, pentoyl-, hexoyl-, heptoyl-, capriloyl-, caproyl-, lauroyl-, myristoyl-, palmitoyl-, stearoyl-, arachidoyl-, behenoyl-, myristoleoyl-, palmitoleoyl-, oleoyl-, linoleoyl-, linolenoyl-, and arachidoneoyl-; and the carbohydrate may be a moiety of glucose, dextrose, maltose, galactose, lactose, sucrose, fructose, or ribose. A preferred alkyl saccharide is decanoyl sucrose.

A cationic surfactant according to the invention means a compound selected from a phosphatidylcholine and lyso phosphatidylcholine, including lyso-myristoyl phosphocholine (LMPC).

An organic acid means naturally occurring acids including methanoic (formic), acetic, caproic, tartaric, citric, benzoic, lactic, propionic, sorbic, malonic, malic, glycolic, and gluconic acids.

Pharmaceutically acceptable diluent means water with or without buffers, salts and the like.

The term "transdermal" means the delivery of an agent into and/or through the skin for local or systemic therapy.

The term "transdermal flux" means the rate of transdermal delivery.

The term "co-delivering" as used herein, means that a supplemental agent(s) is administered transdermally either before the agent is delivered, before and during transdermal flux of the agent, during transdermal flux of the agent, during and after transdermal flux of the agent, and/or after transdermal flux of the agent. Additionally, two or more agents may be coated onto the microprojections resulting in co-delivery of the agents.

The term "biologically active agent" or "active agent" as used herein, refers to a composition of matter or mixture containing a drug which is pharmacologically effective when administered in a therapeutically effective amount.

The term "biologically effective amount" or "biologically effective rate" shall be used when the biologically active agent is a pharmaceutically active agent and refers to the amount or rate of the pharmacologically active agent needed to effect the desired therapeutic, often beneficial, result. The amount of agent employed in the coatings will be that amount necessary to deliver a therapeutically effective amount of the agent to achieve the desired therapeutic result. In practice, this will vary widely depending upon the particular pharmacologically active agent being delivered, the site of delivery, the severity of the condition being treated, the desired therapeutic effect and the dissolution and release kinetics for delivery of the agent from the coating into skin tissues. It is not practical to define a precise range for the therapeutically effective amount of the pharmacologically active agent incorporated into the microneedles and delivered transdermally according to the methods described herein.

The term "stability" shall refer to the property of a formulation to retain its purity level (% (w/w)), within 3% of its starting purity level after a period of time, preferably 0-24 months, 0-12 months, or 0-6 months; at a temperature of 0-50° C., preferably 4-42° C., more preferably 25-40° C.; and at a relative humidity (RH) of 0-100%, preferably 25-85%, more preferably 60-75%. The term "microneedles" refers to piercing elements which are adapted to pierce or cut through the stratum corneum into the underlying epidermis layer, or epidermis and dermis layers, of the skin of a living animal, particularly a human. Typically the piercing elements have a blade length of less than 500 μm, and preferably less than 400 μm. The microprojections typically have a width of about 50 to 200 μm and thickness of about 5 to 50 μm. The microprojections may be formed in different shapes, such as needles, hollow needles, blades, pins, punches, and combinations thereof.

The term "microneedle array" or "microneedle patch" as used herein, refers to a substrate carrying a plurality of microneedles arranged in an array for piercing the stratum corneum. The microneedle patch may be formed by etching or punching a plurality of microneedles from a thin sheet and folding or bending the microneedles out of the plane of the sheet to form a configuration such as that shown in FIG. 1. The microneedle patch may also be formed in other known manners, such as by forming one or more strips having microneedle along an edge of each of the strip(s) as disclosed in U.S. Pat. No. 6,050,988 of the ALZA Corporation, the entire content of which is incorporated herein by reference. The microneedle patch may also include hollow needles which hold a dry pharmacologically active agent.

Liquid and solid dry formulations according to the invention for application to microneedle patches are prepared according to the general procedures of publication Pharm. Res. 27, 303-313 (2010). A liquid glucagon formulation containing a surfactant, an amino acid and an organic acid are prepared according to the following exemplary procedure. Three hundred mg of glucagon is added to 1.5 mL of stock solution containing 50 mg/mL of tartaric acid, 50 mg/mL of glutamine and 100 mg/mL of surfactant. The resultant slurry is then mixed for 2-3 hours or until a clear solution of the liquid formulation is obtained.

A liquid pharmaceutical formulation according to the invention may contain 15-20% (w/w) of glucagon, 7.5-10% (w/w) of a stabilizing agent selected from the group consisting of a cationic or alkyl saccharide surfactant, 3.75-5% (w/w) of an amino acid; 3.75-5% (w/w) of an organic acid, and a pharmaceutically acceptable diluent. The pH of the formulation is adjusted to between 2 and 3.

The dried pharmaceutical formulation on the coated, ready for packaging, patches according to the invention may contain 40-50% (w/w) of glucagon, 20-25% (w/w) of a stabilizing agent selected from either a cationic surfactant or an alkyl saccharide, 10-12.5% (w/w) of an amino acid, 10-12.5% (w/w) of an organic acid. The pH of the formulation is 2 to 3.

The surfactant may be a cationic phospholipid such as lyso-myristoyl phosphatidylcholine. The alkyl saccharide may be sucrose with a C8-C12 alkyl chain such as decanoyl sucrose. The amino acid may be glutamine or glycine. The organic acid may be methanoic acid or tartaric acid.

Figure 2:
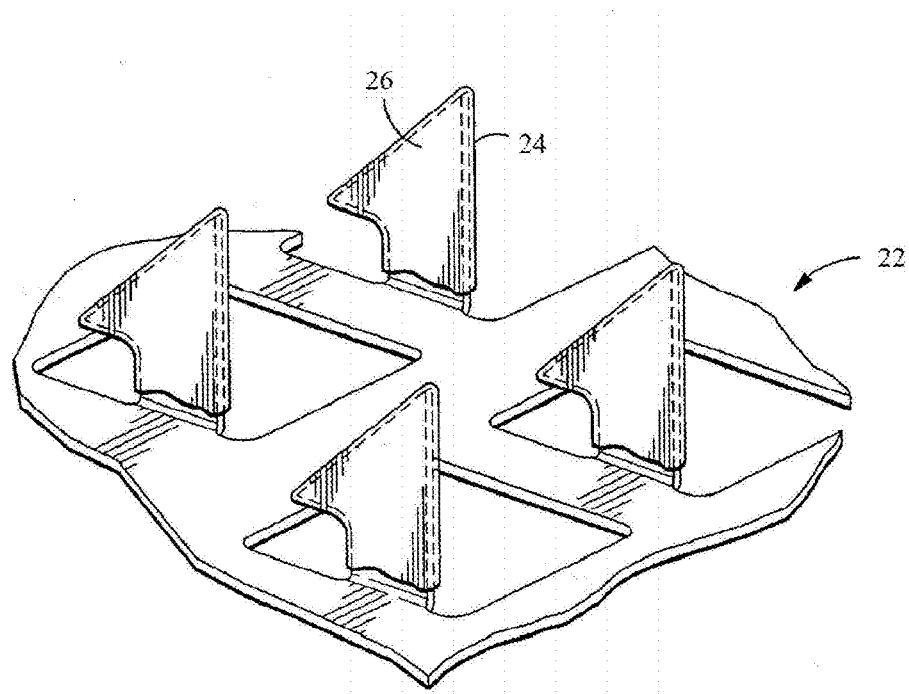
FIG. 2 is a perspective view of the microneedle patch shown in FIG. 1 having a coating deposited on the microneedles, according to the invention.

Embodiments of the present invention provide a formulation containing a biologically active agent, glucagon which when coated and dried upon one or more microneedles of a microneedle patch as shown in FIG. 1, forms a stable coating with enhanced solubilization of the drug upon insertion into the skin for a fast release into the blood stream of the patient and quick treatment onset. Referring to FIG. 1, embodiments of the present invention include a device 22 having a plurality of stratum corneum-piercing microneedles 24 extending therefrom. The microneedles are adapted to pierce through the stratum corneum into the underlying epidermis layer, or epidermis and dermis layers, but do not penetrate so deep as to reach the capillary beds and cause significant bleeding. Referring to FIG. 2, the microneedles carry a coating 26 of the dry formulation of the biologically active agent, glucagon. Upon piercing the stratum corneum layer of the skin, the coating is dissolved by body fluids (intracellular fluids and extracellular fluids such as interstitial fluid) thereby releasing the biologically active agent glucagon into the skin for absorption to the blood stream.

Figure 3:
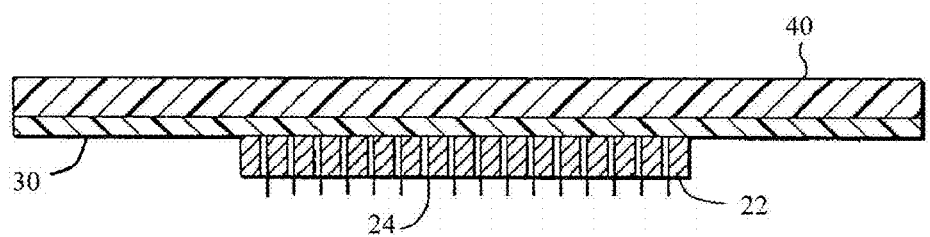
FIG. 3 is a side sectional view of a microneedle patch having an adhesive backing, according to the invention.
Figure 4:
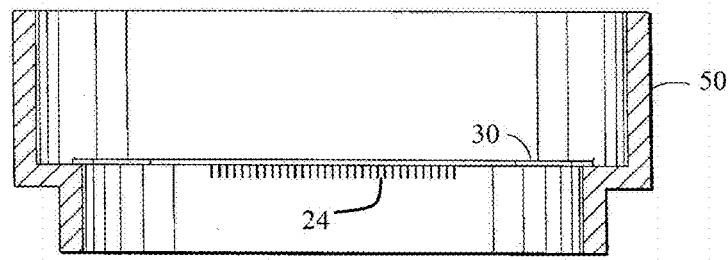
FIG. 4 is a side sectional view of a retainer ring having a microneedle patch disposed therein, according to the invention.
Figure 5:
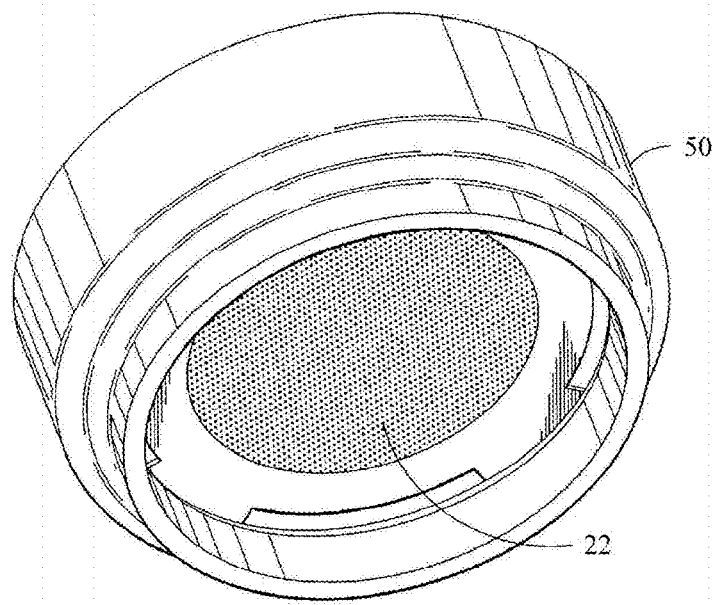
FIG. 5 is a perspective view of the retainer shown in FIG. 4.
Figure 6:
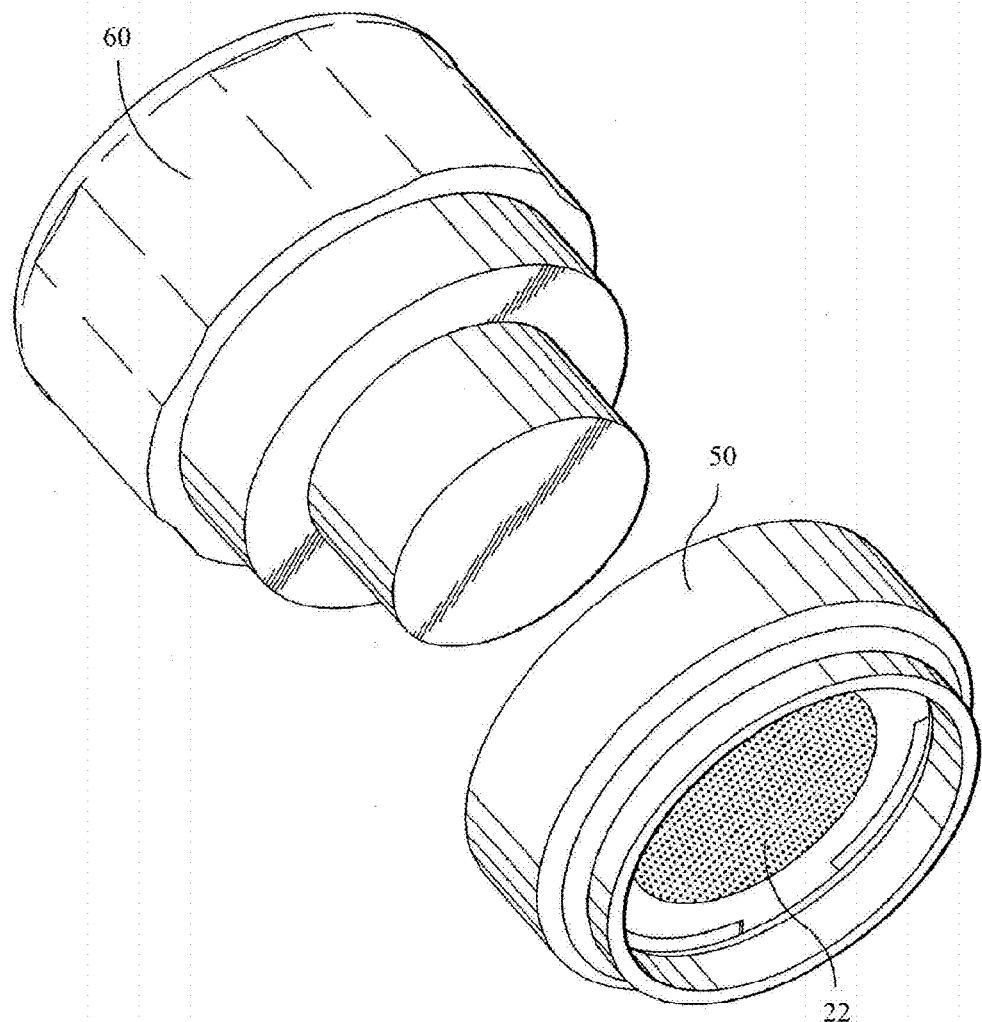
FIG. 6 is an exploded perspective view of an applicator and retainer, according to the invention.
Figure 7:
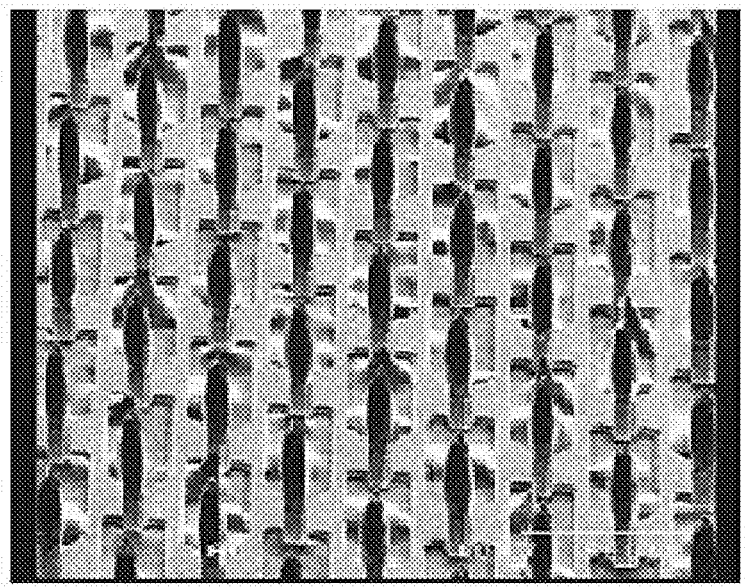
FIG. 7 is an SEM photograph of microneedle patch coated with glucagon according to embodiments of the invention.

The solid coating is obtained by drying a liquid formulation on the microneedles, as described in U.S. Pat. No. 7,537, 795 of the ALZA Corporation, the entire content of which is incorporated herein by reference herein. The liquid formulation is usually an aqueous formulation. In a solid coating on a microneedle patch, the drug is typically present in an amount of 1-2 mg per unit dose. With the addition of formulating agents, the total mass of the solid coating is less than 4 mg per unit dose. The microneedle array 22 is usually present on an adhesive 30 with a backing 40 as shown in FIG. 3, which is attached to a disposable polymeric retainer ring 50 as shown in FIGS. 4 and 5. This assembly is packaged individually in a pouch or a polymeric housing. The microneedle patch 22 is applied to the skin of a patient with the use of a deployment device 60, shown in FIG. 6, on which is mounted the retainer ring 50 with the microneedle patch 22. The deployment device is depressed, detaching the patch 22 from the retainer ring and pushing the microneedles 24 into the skin of the patient. Alternatively the patch can be mounted in a single use applicator ready for patient application, as described in U.S. patent application, 61/864,857 filed Aug. 12, 2013.

Coated microneedle patches for delivery of glucagon may be prepared as follows. Coatings on the microneedles can be formed by a variety of known methods such as dip-coating or spraying. Dip-coating consists of partially or totally immersing the microneedles into a formulation prepared according to the invention. Alternatively, the entire device can be immersed into the formulation. In many instances, it may be preferable to only coat the tips of the microneedles. Microneedles tip coating apparatus and methods are disclosed in U.S. Pat. No. 6,855,372 of the ALZA Corporation, the content of which is incorporated herein by reference in its entirety.

Figure 8:
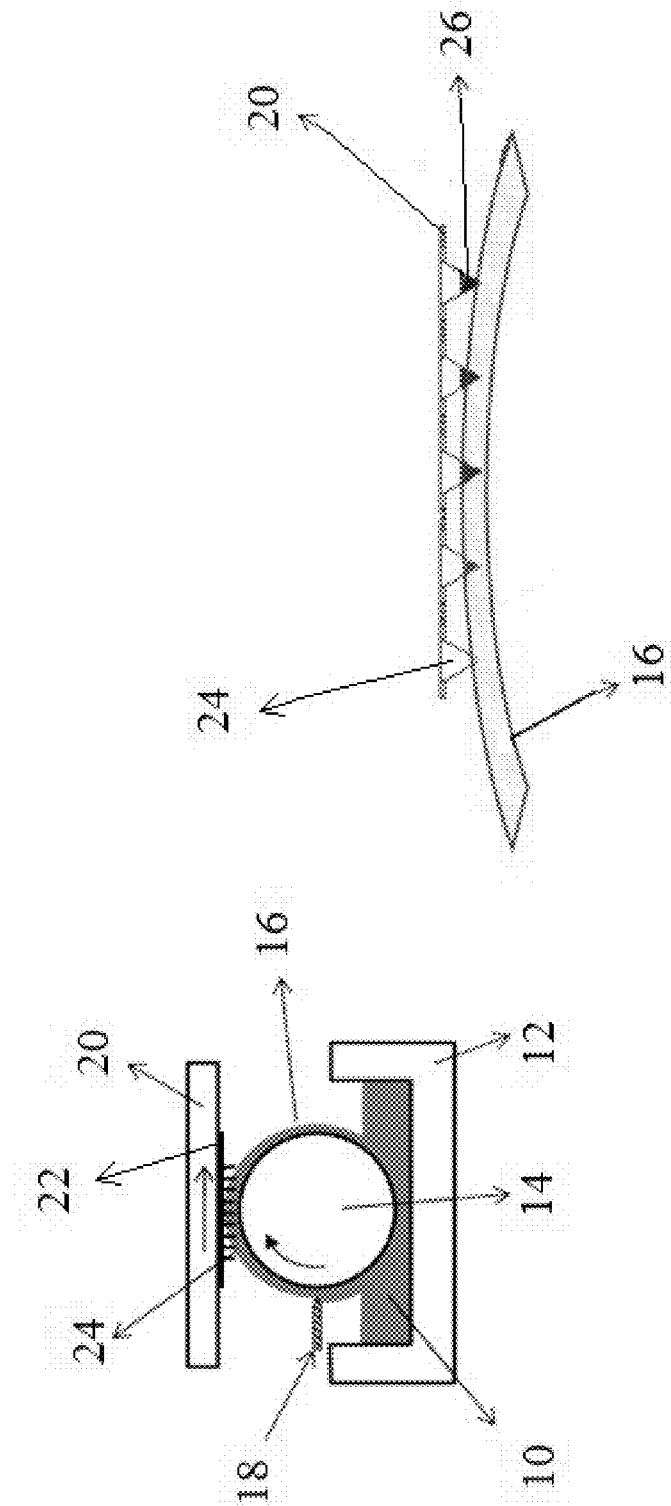
FIGS. 8A and 8B are schematic representations of the process of coating glucagon formulations onto microneedle patches according to an embodiment of the invention.

A sketch of the process is shown in FIG. 8A. The coating apparatus only applies coatings to the microneedles themselves and not upon the substrate that the microneedles project from. A liquid formulation 10 prepared according to the invention is placed into a reservoir 12. A rotating drum 14 is partially submerged into the liquid and is rotated. The liquid 10 forms a thin film on the coating drum 16. A blade 18 controls the thickness of the film to match the length of the microneedles or adjust the dosage on the patches. A sled 20 carrying the substrate 22 with the microneedles 24 is positioned on the drum 14 so that the microneedles 24 are immersed or dipped into the film 16 (shown in the excerpt in FIG. 8B). As the drum 14 rotates, the substrate 22 moves from one side to the other so as to coat the microneedles sequentially. The process can be performed in a continuous manner feeding a series of substrates to the apparatus. The process may be repeated to increase the thickness of the coatings and thus vary the dosage of the patches. This coating technique has the advantage of forming a smooth coating that is not easily dislodged from the microneedles during skin piercing. Other coating techniques such as microfluidic spray or printing techniques can be used to precisely deposit a coating on the microneedles 24.

Dosage of glucagon on the microneedle patches can be controlled by varying a variety of features, such as the size of the patch, the size of the microneedles, the thickness of the coating on the microneedles, and the surface area of the coatings on the microneedles. Patches may thus be prepared for the transdermal delivery of glucagon at the following dose ranges and doses: 0.25-2.0 mg/patch, preferably 0.5-1.0 mg/patch; patch size can be 5 $cm^2$ to 10 $cm^2$ with a microneedle array of 2.5 $cm^2$ to 8 $cm^2$. Treatment of low blood sugar in a patient may require the application of one patch per occurrence. It may also require the application of several patches simultaneously or sequentially until the sugar blood level has reached the normal range of glucose serum concentration.

Techniques for the application of the patches to the skin have been described in U.S. Pat. No. 6,855,131, the content of which is incorporated herein by reference in its entirety. To apply a microneedle patch according to the present invention, a sterile foil package containing the glucagon-loaded patch in a single use, ready to use applicator. The proximal end of the patch/applicator system is pressed against the skin to activate the patch release onto the skin. Within 1-30 minutes, the glucagon is completely released from the patch. The patch may then be removed and discarded.

Physical stabilization, especially minimizing the exposure of the biologically active agent formulations over time to oxidation and hydrolysis, is an important step in assuring efficacy of the therapeutic agents, particularly when the mode of delivery of the therapeutic agent is via a transdermal delivery device having a plurality of microneedles coated with an agent containing biocompatible coating.

Thus, the manufacture and/or packaging of the formulations in a dry inert atmosphere or a partial vacuum, substantially free of oxygen and water, substantially reduces or eliminates undesirable deterioration of the biologically active agent.

The formulations of the present invention display superior stability and are shown to retain substantial purity after storage of up to six months when stored under various temperature and relative humidity conditions. In addition, the formulations of the present invention are shown to remain in predominantly α-helical conformation as a soluble trimer or soluble or soluble helical monomer, as opposed to the β-sheet rich structures found in glucagon fibrils. The superior stability and limited fibril formation of the formulations presented herein offer a significant improvement over currently available glucagon therapeutics.

In one embodiment, the compositions of, and methods for formulating and delivering, biologically active agents are particularly suitable for transdermal delivery using a microneedle delivery device, wherein the biologically active agents are included in a biocompatible coating that is manufactured and/or packaged in a dry inert atmosphere, preferably nitrogen or argon.

In one embodiment, the compositions of, and methods for formulating and delivering, biologically active agents are particularly suitable for transdermal delivery using a microneedle delivery device, wherein the biologically active agents are included in a biocompatible coating that is coated on at least one stratumcorneum piercing microneedle, preferably a plurality of stratumcorneum piercing microneedles of a microneedle delivery device, and manufactured and/or packaged in a dry inert atmosphere, preferably nitrogen or argon.

In one embodiment, the compositions of, and methods for formulating and delivering, biologically active agents are particularly suitable for transdermal delivery using a microneedle delivery device, wherein the biologically active agents are included in a biocompatible coating that is manufactured and/or packaged in a dry inert atmosphere, preferably nitrogen or argon, and in the presence of a desiccant.

In one embodiment, the compositions of, and methods for formulating and delivering, biologically active agents are particularly suitable for transdermal delivery using a microneedle delivery device, wherein the biologically active agents are included in a biocompatible coating that is manufactured and/or packaged in a foil lined chamber having a dry inert atmosphere, preferably nitrogen and a desiccant.

In one embodiment, the compositions of, and methods for formulating and delivering, biologically active agents are particularly suitable for transdermal delivery using a microneedle delivery device, wherein the biologically active agents are included in a biocompatible coating that is manufactured and/or packaged in a partial vacuum.

In one embodiment, the compositions of and methods for formulating and delivering biologically active agents are particularly suitable for transdermal delivery using a microneedle delivery device, wherein the biologically active agents are included in a biocompatible coating that is manufactured and/or packaged in a dry inert atmosphere, preferably nitrogen or a partial vacuum.

In one embodiment, the compositions of and methods for formulating and delivering biologically active agents are particularly suitable for transdermal delivery using a microneedle delivery device, wherein the biologically active agents are included in a biocompatible coating that is manufactured and/or packaged in a foil lined chamber having a dry inert atmosphere, preferably nitrogen and a desiccant.

EXAMPLES

Materials and General Procedures

Glucagon was acquired from BACHEM and was produced by chemical synthesis at a purity of 98.8% (w/w). Formulations of glucagon are prepared following the procedures of publication Pharm. Res. 27, 303-313 (2010). A liquid formulation containing a surfactant, an amino acid and an organic acid was prepared. Three hundred mg of glucagon was added to 1.5 mL of stock solution containing 50 mg/mL tartaric acid, 50 mg/mL glutamine and 100 mg/mL surfactant. The resultant slurry was then mixed for 2-3 hours or until a clear solution of the liquid formulation was obtained.

Physical stability testing of liquid glucagon formulations was conducted utilizing a rheometer (model CVOR150, Bohlin Instrument, Cranbury, N.J.) configured with a cone and plate geometry (a cone angle of 1°and radius 10 mm). Seventy μL of the glucagon liquid formulation was utilized for each experiment. To determine the gel point of a particular glucagon liquid formulation, the sample was sheared at 2667 $s^{-1}$ and viscosities were recorded every 30 seconds. Gelation point was noted at the inflection of the viscosity versus time curve, i.e. at the point where a rapid increase in viscosity was observed.

Example 1

Figure 9:
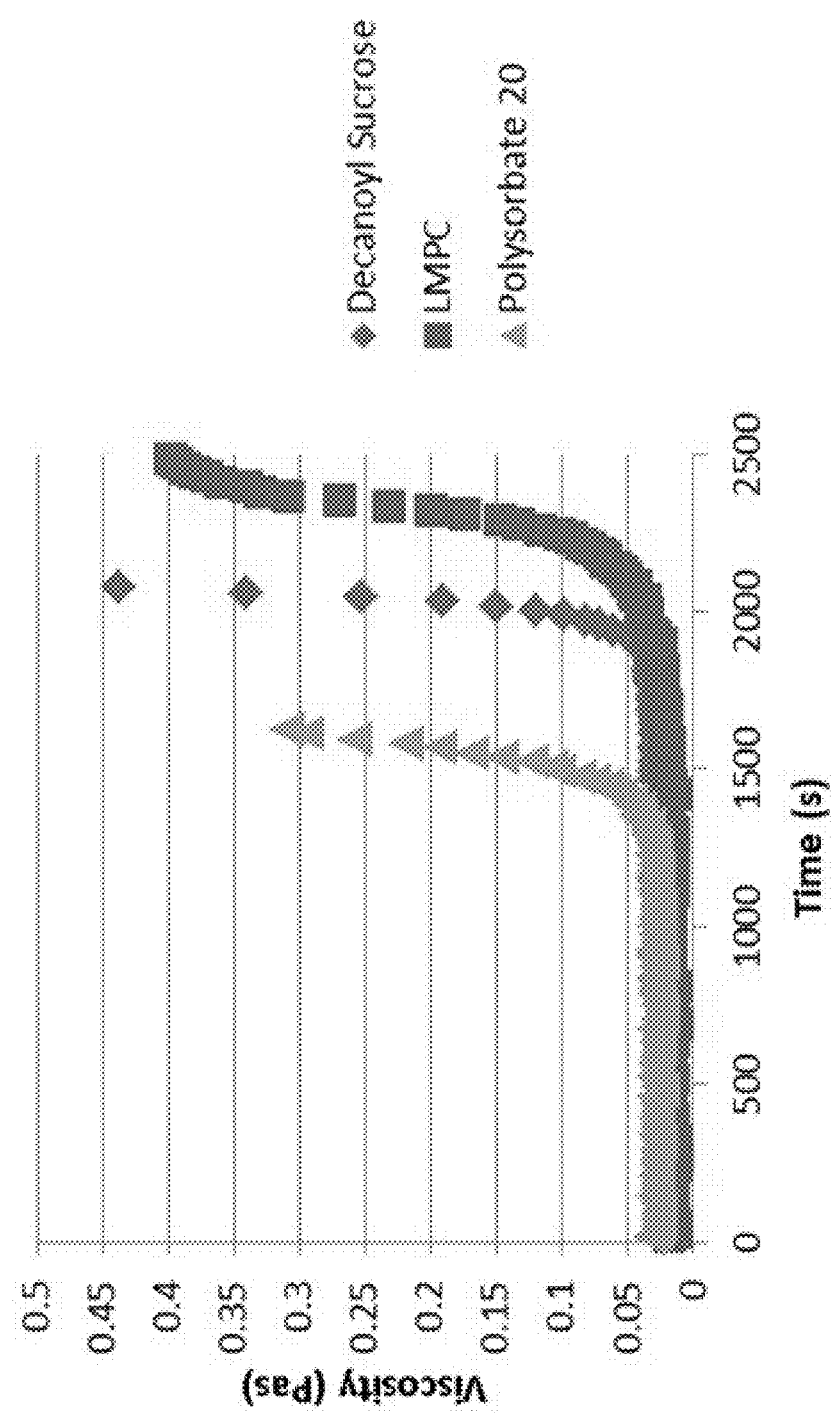
FIG. 9 is a plot of time versus viscosity comparing time to gelation of formulations of glucagon using various stabilizing agents prepared according to Example 1.

Study of the Effect of Surfactants on the Physical Stability of Glucagon Liquid Formulations A summary of the various formulations is shown in Table 1 below. A comparison of the gelation profiles between the formulations is shown in FIG. 9 and gelation point results are shown in Table 1 below.

TABLE 1

| Formulation/ Surfactant | Glucagon (mg/mL) | Surfactant (mg/mL) | Glutamine (mg/mL) | Organic acid (mg/mL) | Gelation point (s) |
| --- | --- | --- | --- | --- | --- |
| Decanoyl Sucrose | 200 | 100 | N/A | 50 | 1800 |
| LMPC | 200 | 100 | N/A | 50 | 1800 |
| Polysorbate 20 | 200 | 2 | N/A | 50 | 1300 |

For a liquid under a fixed shear rate, its viscosity should be constant with time initially and then increase quickly, indicating the point of gelation. The longer it takes to gel, the lower the gelling tendency of a formulation. The viscosity profiles for the three formulations incorporating decanoyl sucrose, LMPC or polysorbate 20 as the surfactant are presented in FIG. 9. All three formulations were sheared at shear rate of 2667 $s^{-1}$ at 8° C. The inflection point (where the viscosity begins to increase) is 1800 seconds for both the decanoyl sucrose and LMPC formulations and 1300 seconds for the polysorbate 20 formulation. It suggests that the decanoyl sucrose and LMPC formulations are less prone to gelation.

Example 2

Figure 10:
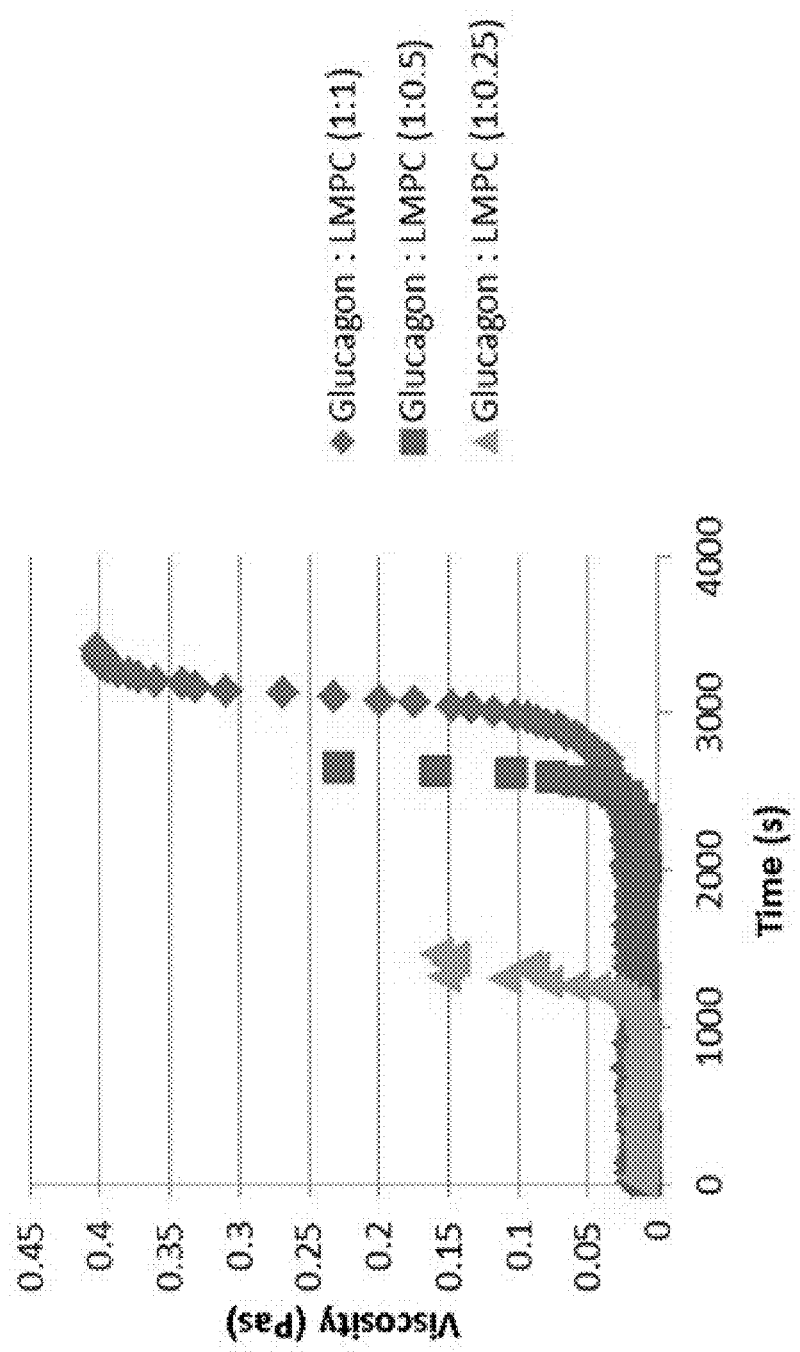
FIG. 10 is a plot of time versus viscosity comparing time to gelation of formulations of glucagon using various concentrations of the stabilizing agents lyso-myristoyl phosphatidylcholine (LMPC) prepared according to Example 2.

Study of the Effect of the Concentration of the Surfactant on the Physical Stability of Glucagon Liquid Formulations A summary of the various formulations is shown in Table 2 below. A comparison of the gelation profiles between the formulations is shown in FIG. 10 and gelation point results are shown in Table 2 below.

TABLE 2

| Formulation/<br>Glucagon:LMPC | Glucagon<br>(mg/mL) | Surfactant<br>(mg/mL) | Glutamine<br>(mg/mL) | Organic<br>acid<br>(mg/mL) | Gelation<br>point (s) |
|---|---|---|---|---|---|
| 1:1 | 200 | 200 | 50 | 50 | 2200 |
| 1:0.5 | 200 | 100 | 50 | 50 | 2200 |
| 1:0.25 | 200 | 50 | 50 | 50 | 1200 |

Results:

The viscosity profiles for the three formulations incorporating LMPC concentrations at 50 mg/mL, 100 mg/mL and 200 mg/mL are presented in FIG. 10. All three formulations were sheared at shear rate of 2667 $s^{-1}$ at 8° C. The inflection point (where the viscosity begins to increase) is 2200 seconds for formulations containing LMPC concentrations of 100 mg/mL and 200 mg/mL (at constant glucagon concentration of 200 mg/mL) and 1200 seconds for the formulation containing LMPC at a concentration of 50 mg/mL. This suggests that a minimum LMPC concentration of 100 mg/mL is required (at a glucagon concentration of 200 mg/mL) is required for a formulation that is less susceptible to gelation.

Example 3

Figure 11:
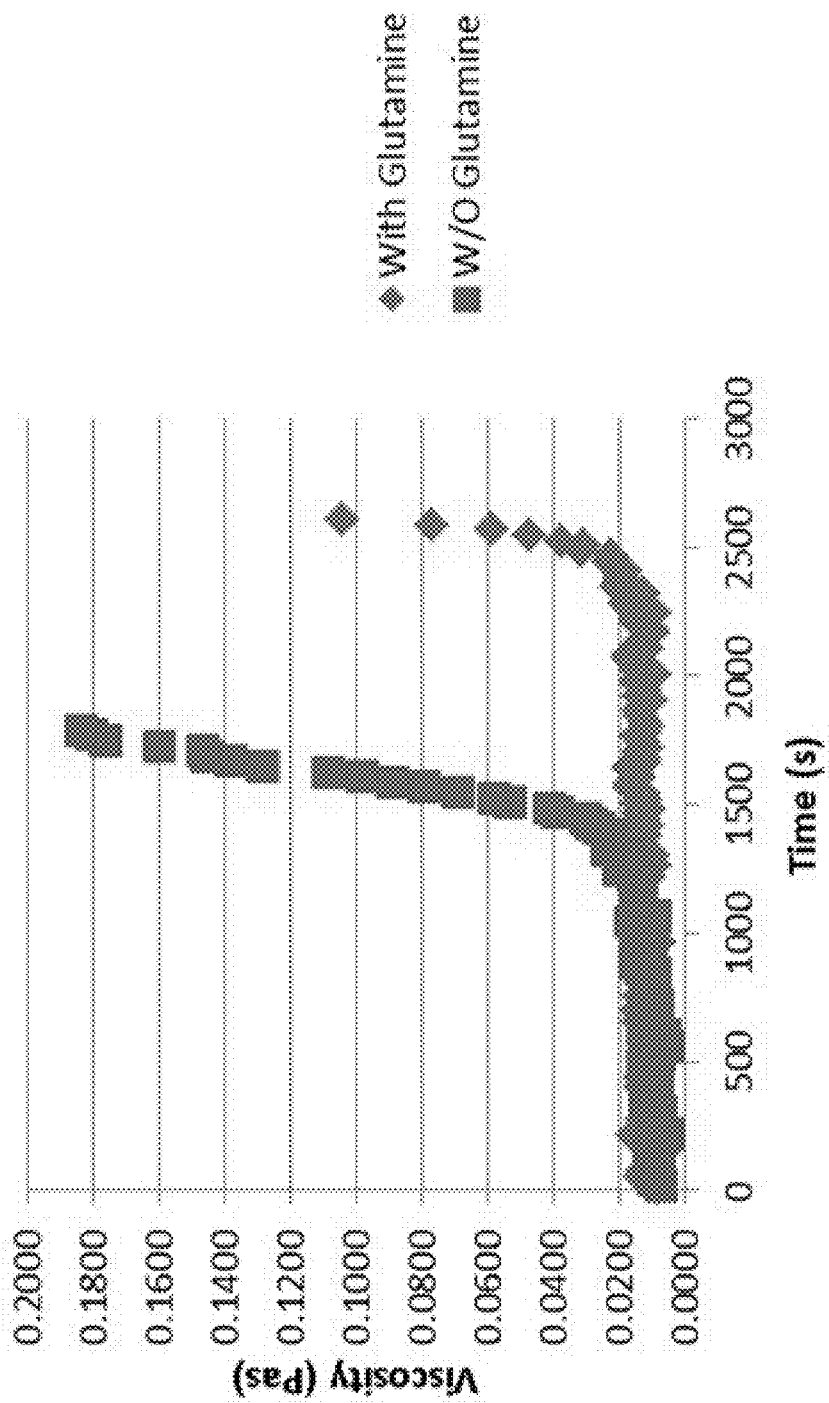
FIG. 11 is a plot of time versus viscosity comparing time to gelation of formulations of glucagon with and without glutamine prepared according to Example 3.

Study of the Effect of Glutamine on the Physical Stability of Glucagon Liquid Formulations A summary of the various formulations is shown in Table 3 below. A comparison of the gelation profiles between the formulations is shown in FIG. 11 and gelation point results are shown in Table 3 below.

TABLE 3

| Formulation/<br>Amino acid | Glucagon<br>(mg/mL) | Surfactant<br>(mg/mL) | Glutamine<br>(mg/mL) | Organic<br>acid<br>(mg/mL) | Gelation<br>point (s) |
|---|---|---|---|---|---|
| Without | 200 | 100 | N/A | 50 | 1400 |
| With Glutamine | 200 | 100 | 50 | 50 | 2200 |

Results:

The viscosity profiles for the two formulations evaluating the effect of glutamine are presented in FIG. 11. The two formulations were sheared at shear rate of 2667 $s^{-1}$ at 8° C. The inflection point (where the viscosity begins to increase) is 2200 seconds for the formulation containing glutamine and 1400 seconds for the formulation containing no glutamine. This result indicates that glutamine is required for a formulation that is less susceptible to gelation.

Example 4

Figure 12:
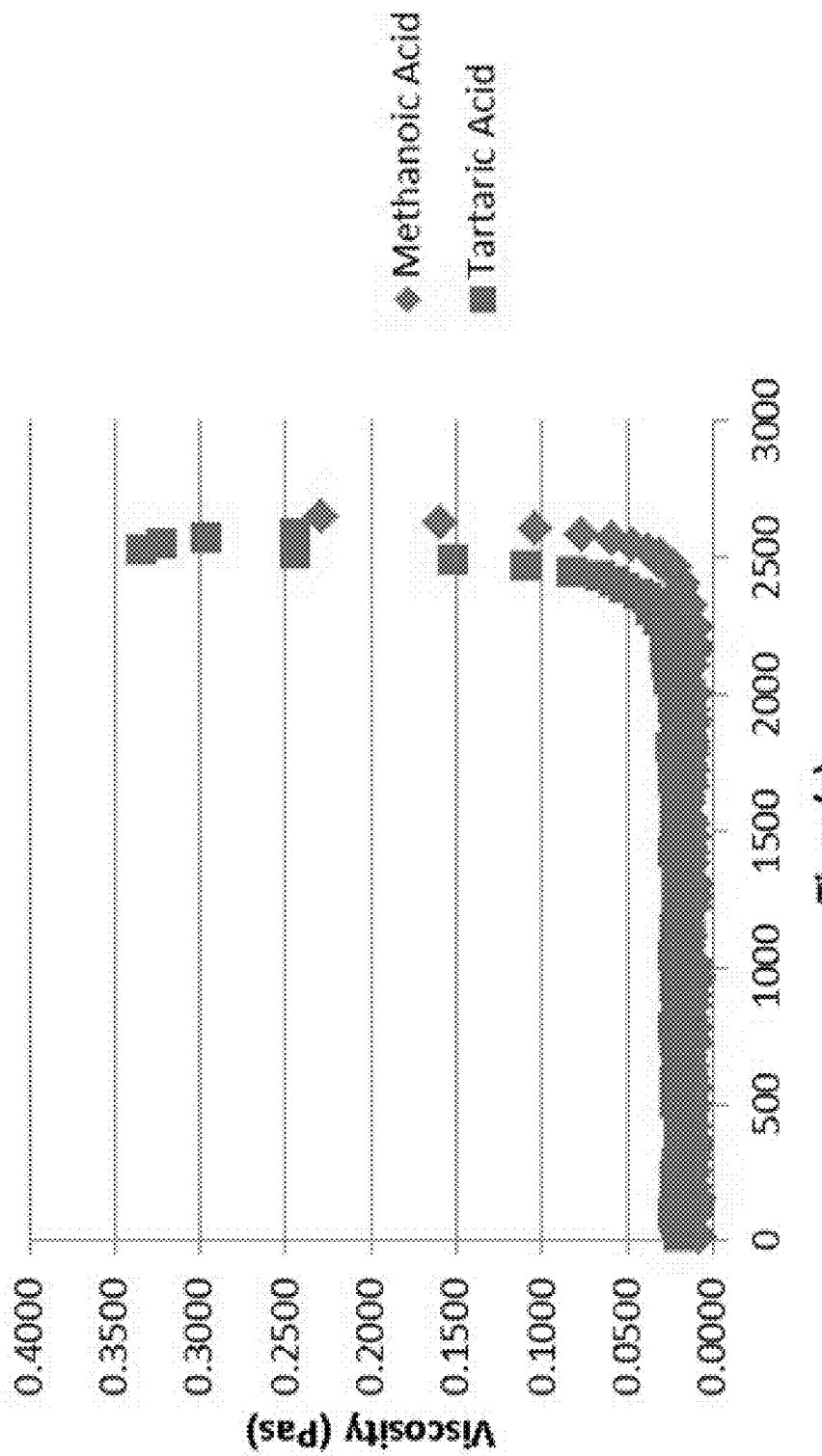
FIG. 12 is a plot of time versus viscosity comparing time to gelation of formulations of glucagon with methanoic or tartaric acid prepared according to Example 4.

Study of the Effect of the Organic Acid on the Physical Stability of Glucagon Liquid Formulations A comparison of the gelation profiles between the formulations is shown in FIG. 12 and gelation point results are shown in Table 4 below.

TABLE 4

| Formulation | Glucagon<br>(mg/mL) | LMPC<br>(mg/mL) | Glutamine<br>(mg/mL) | Organic<br>acid<br>(mg/mL) | Gelation<br>point (s) |
|---|---|---|---|---|---|
| Methanoic acid | 200 | 100 | 50 | 50 | 2200 |
| Tartaric acid | 200 | 100 | 50 | 50 | 2200 |

The viscosity profiles for the two formulations evaluating the effect of tartaric acid and methanoic acid is presented in FIG. 12. The two formulations were sheared at shear rate of 2667 $s^{-1}$ at 8° C. The inflection point (where the viscosity begins to increase) is 2200 seconds for both formulations. This result indicates that methanoic acid and tartaric acid do not adversely affect the physical stability of glucagon formulations.

Example 5

Stability of Glucagon Coatings on Microneedle Patches, Effect of the Organic Acid with LMPC A summary of the various formulations is shown in Table 5 below.

Figure 13:
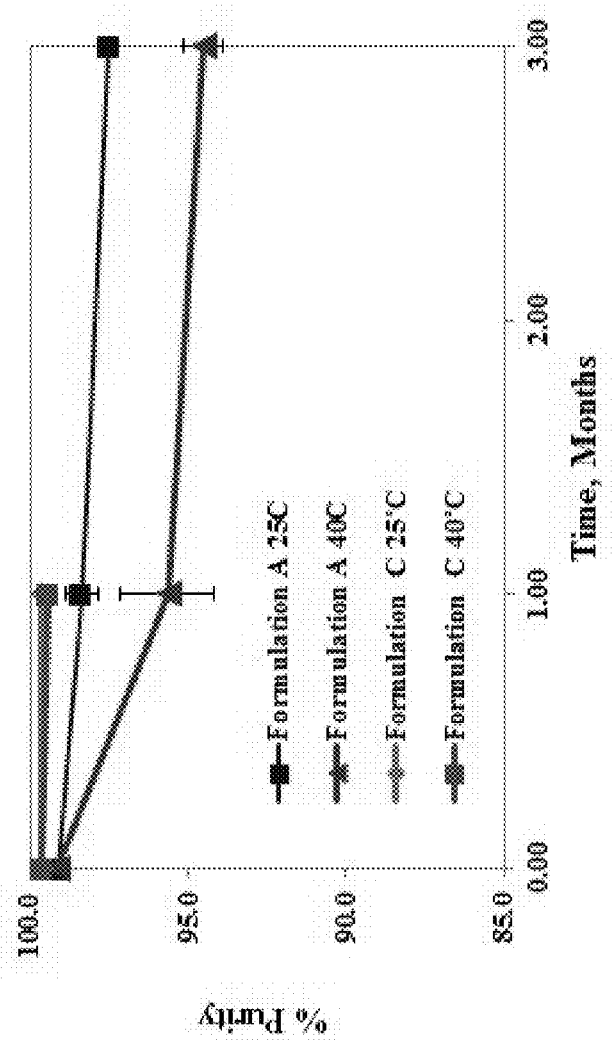
FIG. 13 is a plot of time versus purity comparing stability of formulations of glucagon with glutamine, LMPC and methanoic or tartaric acid prepared according to example 5 at 25° C. and 40° C.

Purity of the glucagon coating was measured at two temperatures: 25° C. and 40° C. The comparison between the formulations is shown in FIG. 13 and results are shown in Tables 6 and 7 below. These results demonstrate the formulation containing tartaric acid show greater stability after three months than the formulation with methanoic acid at both 25° C. and 40° C. temperatures.

TABLE 5

| Formulation | Glucagon<br>(mg/mL) | LMPC<br>(mg/mL) | Glutamine<br>(mg/mL) | Organic<br>acid % |
|---|---|---|---|---|
| A (Methanoic acid) | 200 | 100 | 50 | 5 |
| C (tartaric acid) | 200 | 100 | 50 | 5 |

TABLE 6

Formulation A

| | % (w/w) purity | |
|---|---|---|
| Time (month) | 25° C. | 40° C. |
| 0 | 99.1% ± 0.3 | 99.1 ± 0.3 |
| 1 | 98.4 ± 0.5 | 95.7 ± 1.5 |
| 3 | 97.5 ± 0.1 | 94.5 ± 0.6 |

TABLE 7

Formulation C

| | % (w/w) purity | |
|---|---|---|
| Time (month) | 25° C. | 40° C. |
| 0 | 99.6% ± 0.13 | 99.6 ± 0.13 |
| 1 | 99.6 ± 0.13 | 99.4 ± 0.02 |
| 3 | 99.6 ± 0.03 | 99.4 ± 0.06 |

Example 6

Stability of Glucagon Coatings on Microneedle Patches, Effect of the Organic Acid with Decanoyl Sucrose A summary of the various formulations is shown in Table 8 below.

Figure 14:
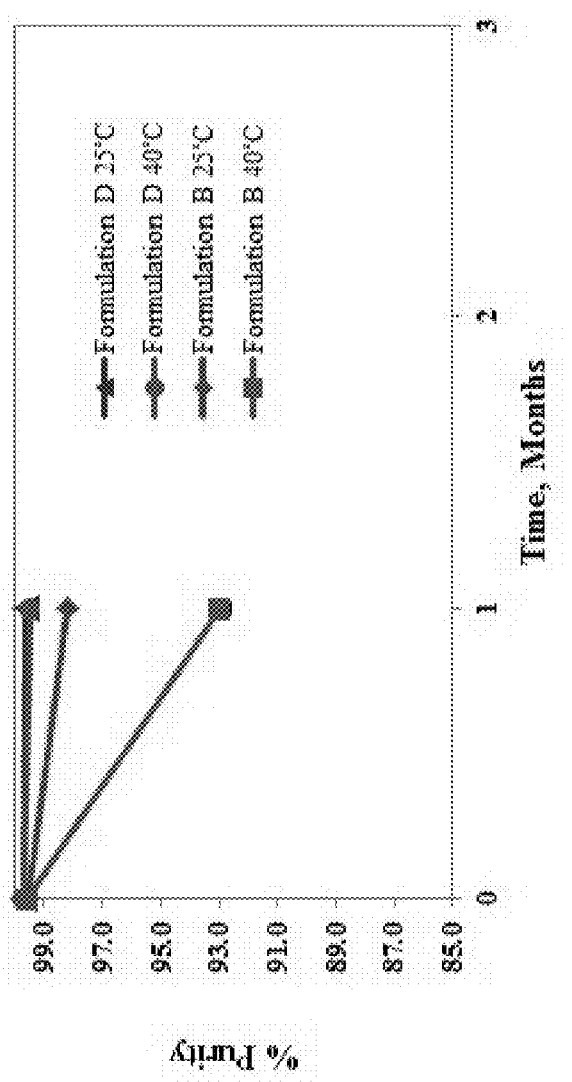
FIG. 14 is a plot of time versus purity comparing stability of formulations of glucagon with glutamine, decanoyl sucrose and methanoic or tartaric acid prepared according to Example 6 at 25° C. and 40° C.

Purity of the glucagon coating was measured at two temperatures: 25° C. and 40° C. The comparison between the formulations is shown in FIG. 14 and results are shown in Tables 9 and 10 below. These results demonstrate the formulation containing tartaric acid show greater stability after one month than the formulation with methanoic acid at both temperatures.

TABLE 8

| Formulation | Glucagon (mg/mL) | Decanoyl sucrose (mg/mL) | Glutamine (mg/mL) | Organic acid % |
|---|---|---|---|---|
| B (methanoic acid) | 200 | 100 | 50 | 5 |
| D (tartaric acid) | 200 | 100 | 50 | 5 |

TABLE 9

Formulation B

| | % (w/w) purity | |
|---|---|---|
| Time (month) | 25° C. | 40° C. |
| 0 | 99.5% ± 0.19 | 99.5 ± 0.19 |
| 1 | 98.2 ± 0.06 | 92.9 ± 0.31 |
| 3 | 92.9 ± 0.31 | 92.4 ± 0.17 |

TABLE 10

Formulation D

| | % (w/w) purity | |
|---|---|---|
| Time (month) | 25° C. | 40° C. |
| 0 | 99.7% ± 0.0 | 99.7 ± 0.0 |
| 1 | 99.6 ± 0.02 | 99.5 ± 0.05 |
| 3 | 99.4 ± 0.07 | 99.2 ± 0.06 |

Example 7

PK Study of Glucagon Coated Microneedle Patches Compared to Subcutaneous Injection In vivo glucagon delivery was performed in a hairless guinea pig model under Institutional Animal Care and Use Committee (IACUC) approved animal protocols. Formulations C and D were coated on microneedle patches at 0.5 mg/3 cm². Patches were applied to the skin and removed after 1 hour. Subcutaneous (SC) glucagon injection was prepared according to manufacturer's instructions (Lilly-Glucagon Rescue Kit®). Both the patch and injection were administered at a dose of 1 mg/kg.

Figure 15:
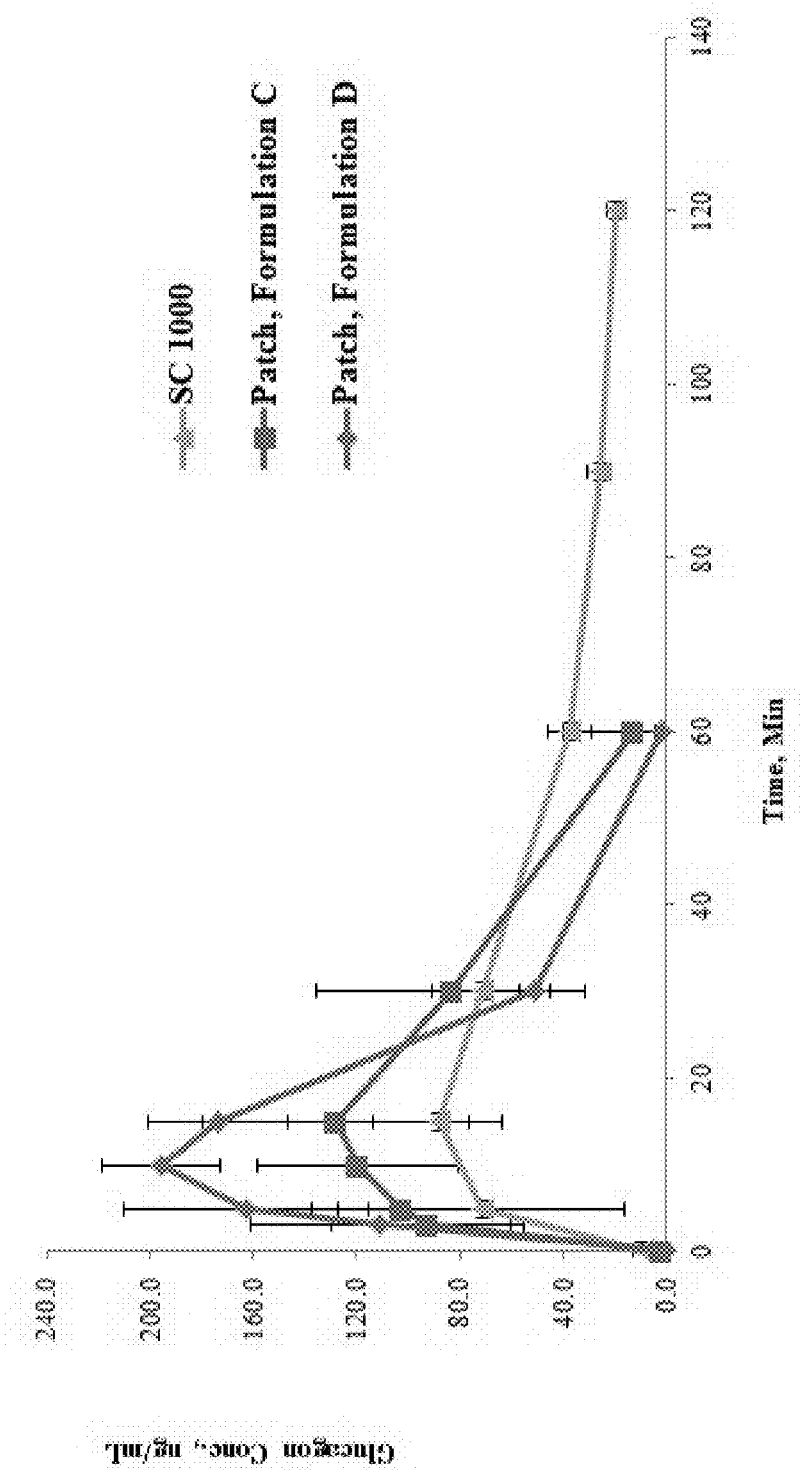
FIG. 15 is a plot comparing the pharmacokinetics of formulations of glucagon on the microneedle patch prepared according to an embodiment of the invention versus subcutaneous injection in the hairless guinea pig, detailed at Example 7.

As shown in FIG. 15, coatings of the formulation C and D provide the fast and high release of glucagon as measured in the serum levels. Table 11 shows that the bioavailability of glucagon delivery with formulation C or D coated microneedle patch is 83% and 86%, respectively of that observed with SC injection. This indicates that the glucagon formulations can be efficiently re-solubilized in the skin and glucagon delivered comparable to the commercially available glucagon injection.

TABLE 11

| Treatment | Dose (μg)/Animal | Dose per kg Body Weight (μg/kg) | Delivery Efficiency (%) | Mean $T_{max}$ (minutes) | Mean $C_{max}$ (ng/ml) | Mean $AUC_t$ (ng · h/ml) |
|---|---|---|---|---|---|---|
| SC injection | 424 | 1000 | N/A | 9 | 95 | 91 |
| ZP Glucagon Patch, C 0.5 mg/3 cm² | 497 | 956 | 69 | 13 | 135 | 76 |
| ZP Glucagon Patch, D 0.5 mg/3 cm² | 536 | 957 | 65 | 10 | 202 | 79 |

The embodiments of the invention described above are intended to be merely exemplary; numerous variations and modifications will be apparent to those skilled in the art. All such variations and modifications are intended to be within the scope of the present invention as defined in any appended claims.

Example 8

Stability of Glucagon Coatings on Microneedle Patch

Two glucagon liquid formulations were prepared. Formulation 1 comprises 200 mg/mL glucagon, 100 mg/mL LMPC (1-myristoyl-2-hydroxy-sn-glycero-3-phosphocholine), 50 mg/mL glutamine, and 50 mg/mL tartaric acid; Formulation 2 comprises 200 mg/mL glucagon, 100 mg/mL decanoyl sucrose (DS), 50 mg/mL glutamine, and 50 mg/mL tartaric acid.

Each glucagon liquid formulation was coated on a microneedle array using a dip coating method. After coating glucagon systems were manufactured for stability studies, using patch components involving a polycarbonate retainer ring with co-molded desiccant and a 5 cm² adhesive patch. The coated patch was heat sealed in a nitrogen-purged foil pouch. The final systems were stored under two conditions, 25° C./60% relative humidity (RH) and 40° C./75% RH. The coated patches were assessed for purity at initial, 1-, 3-, and 6-month time points.

RP-HPLC was used to quantify purity of glucagon. Glucagon related impurities were separated from native glucagon using an ACE C18 column (3.0 mm ID×150 mm, 3 µm) maintained at 45° C. The eluted glucagon was detected by UV at 214 nm. The mobile phase involved a gradient elution. Mobile phase A comprised of 80% 0.15 M phosphate buffer at pH=2.7, 20% acetonitrile; mobile phase B comprised of 60% water and 40% acetonitrile. Chromatography was performed with an HPLC system (Waters 2695 Alliance, Milford Mass.) provided with a binary pump, a thermostatted autosampler, a thermostatted column compartment, and a 996 PAD. Data were collected and analyzed using Empower.

Figure 16:
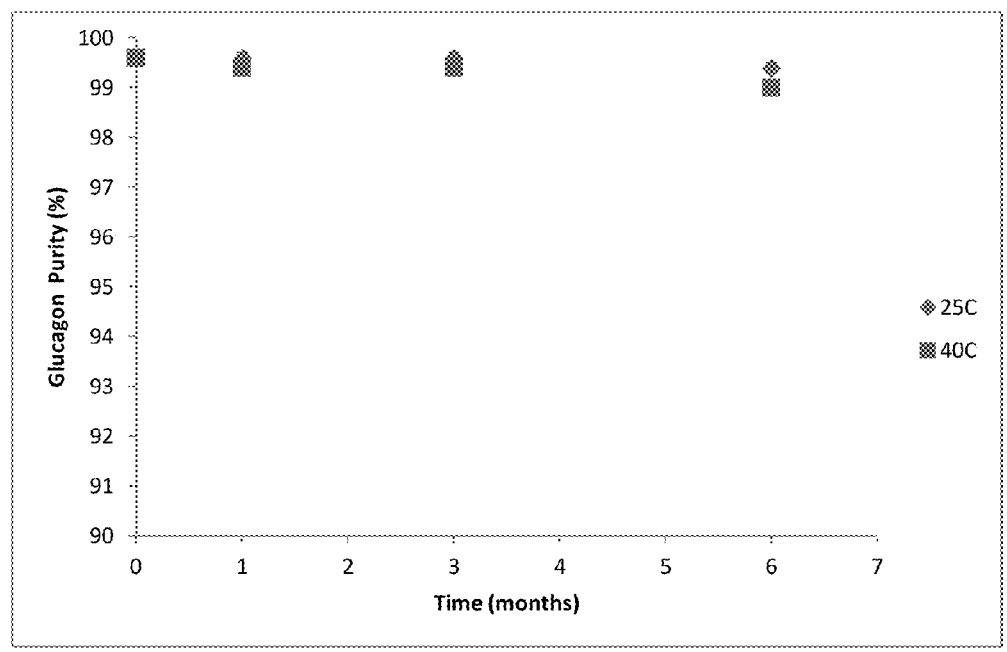
FIG. 16 is a plot comparing purity over time for Formulation 1. The plot shows the stability of glucagon systems where the titanium array was coated Formulation 1 with 0.5 mg of glucagon, assembled with a polycarbonate retainer ring with a co-molded desiccant and a 5 cm² adhesive patch, and heat sealed in a nitrogen-purged foil pouch.
Figure 17:
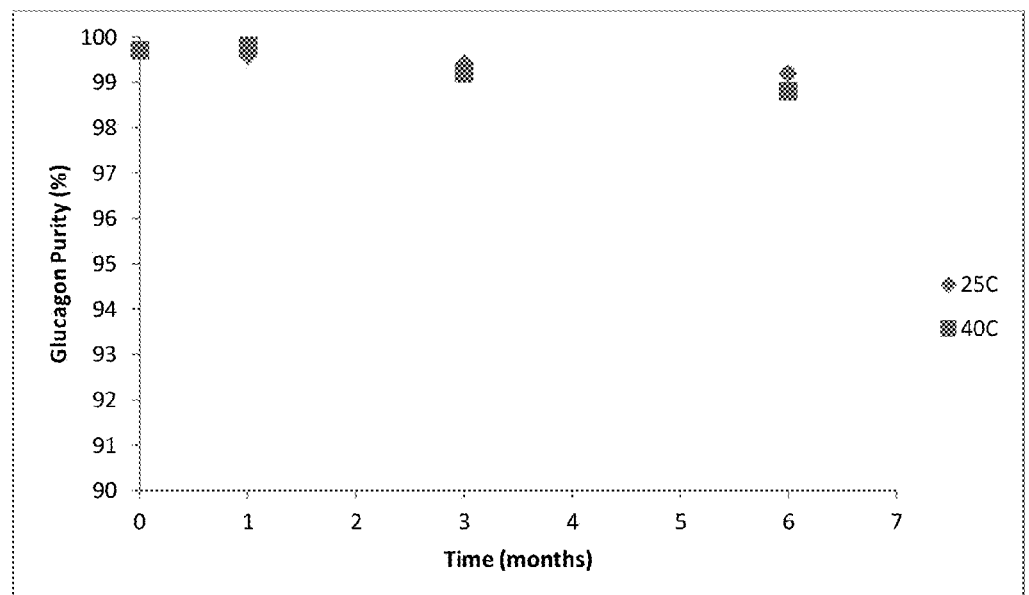
FIG. 17 is a plot comparing purity over time for Formulation 2. The plot shows the stability of glucagon systems where the titanium array was coated Formulation 1 with 0.5 mg of glucagon, assembled with a polycarbonate retainer ring with a co-molded desiccant and a 5 cm² adhesive patch, and heat sealed in a nitrogen-purged foil pouch.

The stability data is shown in FIGS. 16 and 17 for Formulations 1 and 2 respectively. Table 12 summarizes the purity data of the two formulations under the two storage conditions. Under the accelerated conditions of 40° C./75% RH and when stored at 25° C./60% RH, glucagon maintained excellent stability within the study period.

NKTT120 Protein Concentration by OD280 Measurements

The protein concentration in solution was determined by measurement of OD280. An extinction coefficient was calculated based on the molecular weight and contributions by the aromatic amino acids. All measurements were performed on a Varian Cary 100 UV/Vis spectrophotometer. The calculated molar extinction coefficient of 8480 $M^{-1}$ $cm^{-1}$ was used to determine an estimated specific extinction coefficient of E2 so, tcm=2.43 (based on a molecular weight of 3482.8 kDa). Correction for light scattering was made by subtracting the absorbance at 320 nm.

Circular Dichroism Spectroscopy

An Aviv Model 202 with a peltier controlled temperature controlled cell was used to collect all CD spectra. All spectra were collected at 25° C. in quartz cuvettes. The quartz cuvettes were tested using camphorsulfonic acid (CSA) to measure accurate path lengths for all cells used. The 0.1 mm cell was measured at 0.089 mm, and the 0.01 mm cell was measured at 0.0165 mm. All CD spectra are reported in units

TABLE 12

Summary of stability data of glucagon coated systems

| Formulation | Formulation Composition (Respective Amounts (mg/ml)) | Temperature (° C.) | Glucagon purity (%(w/w)) | | | |
|---|---|---|---|---|---|---|
| | | | Initial | 1 Month | 3 Months | 6 Months |
| 1 | Tartaric acid + Glutamine + LMPC | 25 | 99.6 ± 0.1 | 99.6 ± 0.1 | 99.6 ± 0.0 | 99.4 ± 0.14 |
| | (50 mg/ml + 50 mg/ml + 100 mg/ml) | 40 | 99.6 ± 0.1 | 99.4 ± 0.0 | 99.4 ± 0.1 | 99.0 ± 0.08 |
| 2 | Tartaric acid + Glutamine + DS | 25 | 99.7 ± 0.0 | 99.6 ± 0.0 | 99.4 ± 0.1 | 99.4 ± 0.02 |
| | (50 mg/ml + 50 mg/ml + 100 mg/ml) | 40 | 99.7 ± 0.0 | 99.5 ± 0.1 | 99.2 ± 0.1 | 98.8 ± 0.02 |

Example 9

Far-UV Circular Dichroism Spectra of Glucagon Coated Patches

Patch C coated with formulation 1, and Patch D coated with Formulation 2, were each placed into a separate extraction vessel and 1.0 mL of dissolution solution was added to each vessel. Each solution was then agitated for 2 minutes and a sample was taken for circular dichroism (CD) spectroscopy. Each sample was also scanned for OD280 (optical density at a wavelength of 280 nm) in a 1 mm quartz cuvette.

of mean residue ellipticity (θ) using a molecular weight of 3482.8 kDa and 29 residues.

Figure 18:
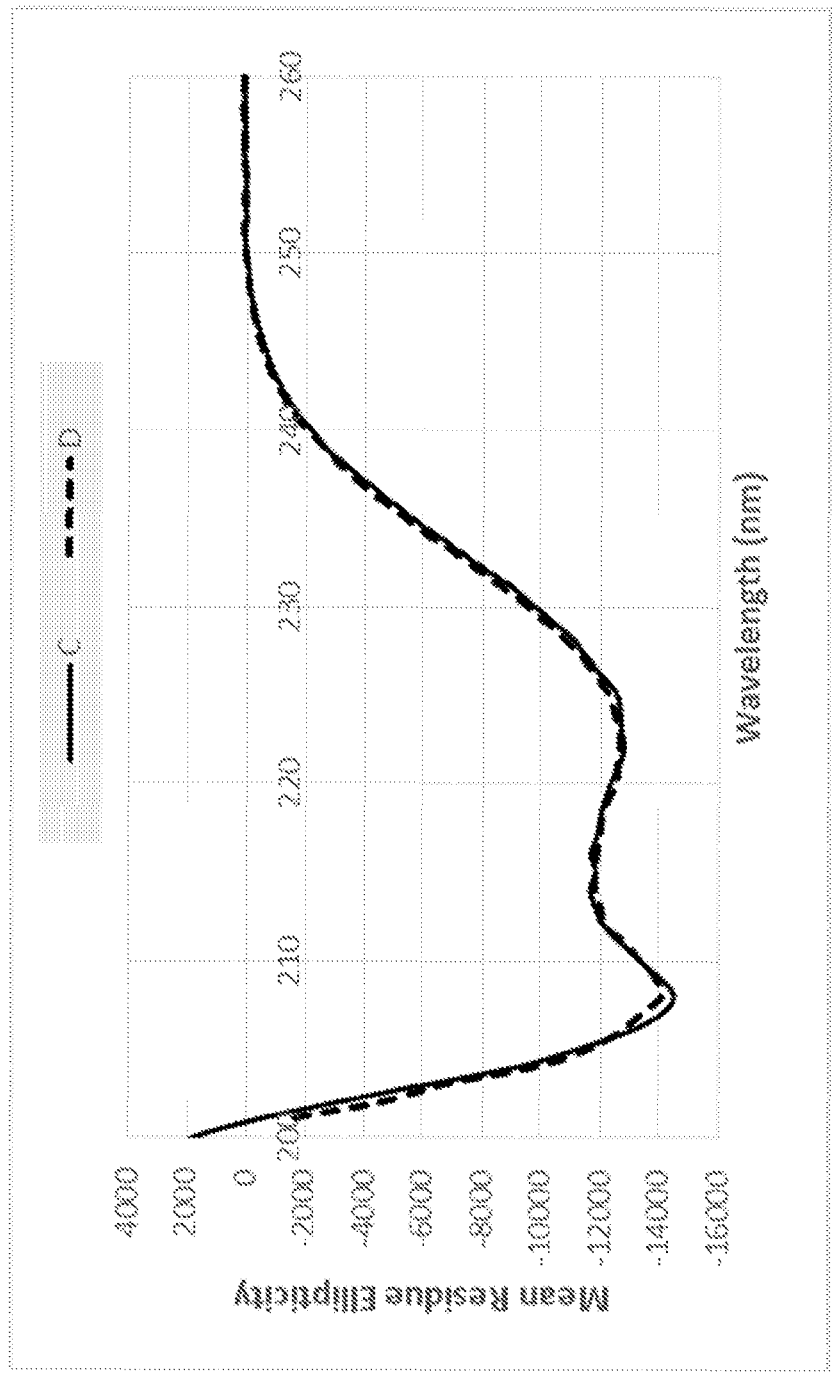
FIG. 18 shows the Far UV (FUV) circular dichroism (CD) spectra for glucagon extracted from Patch C and Patch D. ZP-Glucagon patches were evaluated for glucagon fibrillation by CD after glucagon dissolution. These CD spectra are consistent with a glucagon peptide in a predominantly α-helical conformation as a soluble trimer or soluble helical monomer, as opposed to the β-sheet rich structure in glucagon fibrils. As there is still a significant amount of random coil structure, this is also consistent with monomeric glucagon.

The Far UV (FUV) circular dichroism (CD) spectra for glucagon extracted from two patches (Patch C and Patch D), shown in FIG. 18, are consistent with a glucagon peptide in a predominantly α-helical conformation as a soluble trimer or soluble helical monomer, as opposed to the β-sheet rich structure in glucagon fibrils. The spectra are also consistent with a peptide in a soluble trimer or soluble helical monomer. As there is still a significant amount of random coil structure, this is also consistent with monomeric glucagon.

What is claimed is:

1. A liquid pharmaceutical formulation comprising
   a. 15-20% (w/w) of glucagon;
   b. 7.5-10% (w/w) of a stabilizing agent selected from either a cationic or neutral surfactant;
   c. 3.75-5% (w/w) of an amino acid;
   d. 3.75-5% (w/w) of an organic acid; and
   e. a pharmaceutically acceptable diluent; and
   wherein the formulation has a pH between 2 and 3.

2. A liquid pharmaceutical formulation comprising
   a. 15-20% (w/w) of glucagon;
   b. 7.5-10% (w/w) of a stabilizing agent comprising a surfactant that is a phospholipid;
   c. 3.75-5% (w/w) of an amino acid;
   d. 3.75-5% (w/w) of an organic acid; and
   e. a pharmaceutically acceptable diluent; and
   wherein the formulation has a pH between 2 and 3.

3. The pharmaceutical formulation according to claim 2, wherein the phospholipid is lyso-myristoyl phosphatidylcholine.

4. The pharmaceutical formulation according to claim 1, wherein the surfactant is decanoyl sucrose.

5. The pharmaceutical formulation according to claim 1, wherein the amino acid is selected from the group consisting of glutamine and glycine.

6. The pharmaceutical formulation according to claim 1, which has a viscosity in the range of 20-200 cP.

7. The pharmaceutical formulation according to claim 1, wherein the organic acid is selected from the group consisting of methanoic acid, ethanoic acid, tartaric acid, malonic acid, glycolic acid, malic acid, gluconic acid, citric acid, caproic acid, benzoic acid, lactic acid, propionic acid, and sorbic acid.

8. The pharmaceutical formulation according to claim 1, wherein the surfactant is decanoyl sucrose, the amino acid is glutamine and the organic acid is tartaric acid.

9. The pharmaceutical formulation according to claim 1, wherein the surfactant is decanoyl sucrose, the amino acid is glycine and the organic acid is tartaric acid.

10. The pharmaceutical formulation according to claim 1, wherein the surfactant is lyso-myristoyl phosphatidylcholine, the amino acid is glutamine and the organic acid is tartaric acid.

11. The pharmaceutical formulation according to claim 1, wherein the surfactant is lyso-myristoyl phosphatidylcholine, the amino acid is glycine and the organic acid is tartaric acid.

12. A solid pharmaceutical formulation comprising
    a. 40-50% (w/w) of glucagon or a glucagon-like peptide;
    b. 20-25% (w/w) of a stabilizing agent selected from either a cationic or neutral surfactant;
    c. 10-12.5% (w/w) of an amino acid;
    d. 10-12.5% (w/w) of an organic acid; and wherein the formulation has a pH between 2 and 3.

13. A solid pharmaceutical formulation comprising
    a. 40-50% (w/w) of glucagon or a glucagon-like peptide;
    b. 20-25% (w/w) of a stabilizing agent comprising a surfactant that is a phospholipid;
    c. 10-12.5% (w/w) of an amino acid;
    d. 10-12.5% (w/w) of an organic acid; and
    wherein the formulation has a pH between 2 and 3.

14. The pharmaceutical formulation according to claim 13, wherein the phospholipid is lyso-myristoyl phosphatidylcholine.

15. The pharmaceutical formulation according to claim 12, wherein the surfactant is selected from the group consisting of glucose, sucrose, trehalose, and dextrose, wherein said surfactant is substituted with a C8-C12 alkyl chain.

16. The pharmaceutical formulation according to claim 12, wherein the amino acid is selected from the group consisting of glutamine and glycine.

17. The pharmaceutical formulation according to claim 12, wherein the organic acid is selected from the group consisting of methanoic acid, ethanoic acid, tartaric acid, malonic acid, glycolic acid, malic acid, gluconic acid, and citric acid.

18. The pharmaceutical formulation according to claim 12, wherein the surfactant is decanoyl sucrose, the amino acid is glutamine and the organic acid is tartaric acid.

19. The pharmaceutical formulation according to claim 12, wherein the surfactant is decanoyl sucrose, the amino acid is glycine and the organic acid is tartaric acid.

20. The pharmaceutical formulation according to claim 12, wherein the surfactant is lyso-myristoyl phosphatidylcholine, the amino acid is glutamine and the organic acid is tartaric acid.

21. The pharmaceutical formulation according to claim 12, wherein the surfactant is lyso-myristoyl phosphatidylcholine, the amino acid is glycine and the organic acid is tartaric acid.

22. A medical device for the delivery of a pharmaceutical agent through the skin, the device comprising an array of microneedles having coated thereon a liquid pharmaceutical formulation according to claim 1.

23. The medical device of claim 22 carrying a therapeutic dose of glucagon selected from the group consisting of 0.25 mg, 0.5 mg, and 1 mg.

24. A medical device for the delivery of a pharmaceutical agent through the skin, the device comprising an array of microneedles having coated thereon a solid pharmaceutical formulation according to claim 12.

25. The medical device of claim 24 carrying a dose of glucagon selected from the group consisting of 0.25 mg 0.5 mg, and 1 mg.

26. The medical device of claim 24, wherein once applied to the skin of a patient the coating is dissolved by the body fluids of the patient in less than 30 minutes.

27. The medical device of claim 26, wherein once applied to the skin of a patient the coating is dissolved by the body fluids of the patient in less than 20 minutes.

28. The medical device of claim 24, wherein once applied to the skin of a patient the coating is dissolved by the body fluids of the patient in less than 10 minutes.

29. A process for coating a medical device comprising:
    a. coating a liquid pharmaceutical formulation according to claim 1 onto a medical device; and
    b. drying the liquid pharmaceutical formulation.

30. A method of treating a patient having a low blood sugar comprising applying the medical device of claim 24 to the skin of the patient.

31. The method of claim 30, wherein a blood serum $C_{max}$ of glucagon is reached in less than 30 minutes.

32. The method of claim 30, wherein a blood serum $C_{max}$ of glucagon is reached in about 10 minutes.

33. The method of claim 30, wherein a blood serum $C_{max}$ of glucagon reaches at least 5 ng/mL.

34. The method of claim 30, wherein a blood serum $C_{max}$ of glucagon reaches at least 10 ng/mL.

35. The method of claim 30, wherein a blood serum $C_{max}$ of glucagon reaches about 20 ng/mL.

36. The method of claim 30, wherein a blood serum $C_{max}$ of glucagon of at least 5 ng/mL is reached in about 10 minutes following application of the device to the skin of the patient.

37. The method of claim 30, wherein a blood serum $C_{max}$ of glucagon of about 10 ng/mL is reached in about 10 minutes following application of the device to the skin of the patient.

38. The method of claim 30, wherein a blood serum concentration of glucagon is less than 10 ng/mL at about 60 minutes following application of the device to the skin of the patient.

39. The method of claim 36, wherein the blood serum concentration of glucagon is less than 10 ng/mL at about 40 minutes following application of the device to the skin of the patient.

40. The method of claim 37, wherein the blood serum concentration of glucagon is less than 10 ng/mL at about 30 minutes following application of the device to the skin of the patient.

41. The pharmaceutical formulation according to claim 1, wherein the stability of said pharmaceutical formulation is maintained after storage at a temperature of 0-50° C. and a relative humidity of 0-100%.

42. The pharmaceutical formulation according to claim 41, wherein said temperature is 4-42° C.

43. The pharmaceutical formulation according to claim 42, wherein said temperature is 25-40° C.

44. The pharmaceutical formulation according to any one of claims 41, 42, and 43, wherein said relative humidity is 25-85%.

45. The pharmaceutical formulation according to any one of claims 41, 42, and 43, wherein said relative humidity is 60-75%.

* * * * *

SEQUENCE LISTING

```
<160> NUMBER OF SEQ ID NOS: 1

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```